United States Patent [19]

Chan

[11] 4,269,849

[45] May 26, 1981

[54] FUNGICIDAL 3-(N-CYCLOALKYLCARBONYL-N-ARYLAMINO)-GAMMA-BUTYROLACTONES AND GAMMA-BUTYROTHIOLACTONES

[75] Inventor: David C. K. Chan, Petaluma, Calif.

[73] Assignee: Chevron Research Company, San Francisco, Calif.

[21] Appl. No.: 102,793

[22] Filed: Dec. 12, 1979

Related U.S. Application Data

[63] Continuation-in-part of Ser. No. 13,856, Feb. 22, 1979, which is a continuation-in-part of Ser. No. 847,502, Nov. 1, 1977, abandoned, which is a continuation-in-part of Ser. No. 837,121, Sep. 29, 1977, Pat. No. 4,141,989, which is a continuation-in-part of Ser. No. 731,491, Oct. 12, 1976, Pat. No. 4,107,323, which is a continuation-in-part of Ser. No. 631,351, Nov. 12, 1978, Pat. No. 4,012,519, which is a continuation-in-part of Ser. No. 548,660, Feb. 10, 1975, Pat. No. 3,933,860.

[51] Int. Cl.³ ............................................. A01N 43/02
[52] U.S. Cl. ..................................................... 424/275
[58] Field of Search .......................... 549/63; 424/275

[56] References Cited

U.S. PATENT DOCUMENTS

| | | | |
|---|---|---|---|
| 4,021,433 | 5/1977 | Cavazza | 424/266 |
| 4,072,703 | 2/1978 | Blum | 549/63 X |
| 4,082,771 | 4/1978 | Evans et al. | 549/69 |
| 4,165,322 | 8/1979 | Reynolds, Jr. | 549/63 X |
| 4,187,232 | 2/1980 | Evans et al. | 549/69 |
| 4,203,904 | 5/1980 | Reynolds, Jr. | 549/63 X |

FOREIGN PATENT DOCUMENTS 767244 11/1971 Belgium ..................................... 549/69

OTHER PUBLICATIONS

Chem. Abstracts 86:190460w.

*Primary Examiner*—Ethel G. Love
*Attorney, Agent, or Firm*—D. A. Newell; T. G. DeJonghe; R. J. Suyat

[57] ABSTRACT

3-(N-cycloalkylcarbonyl-N-arylamino)-gamma-butyrolactones, thiobutyrolactones and butyrolactams have fungicidal activity.

11 Claims, No Drawings

FUNGICIDAL 3-(N-CYCLOALKYLCARBONYL-N-ARYLAMINO)-GAMMA-BUTYROLACTONES AND GAMMA-BUTYROTHIOLACTONES

RELATED APPLICATIONS

This application is a continuation-in-part of application Ser. No. 13,856, filed Feb. 22, 1979, which in turn is a continuation-in-part of Ser. No. 847,502, filed Nov. 1, 1977, now abandoned which in turn is a continuation-in-part of application Ser. No. 837,121, filed Sept. 29, 1977, now U.S. Pat. No. 4,141,989 which in turn is a continuation-in-part of application Ser. No. 731,491, filed Oct. 12, 1976, now U.S. Pat. No. 4,107,323, which in turn is a continuation-in-part of application Ser. No. 631,351, filed Nov. 12, 1975, now U.S. Pat. No. 4,012,519, which in turn is a continuation-in-part of application Ser. No. 548,660, filed Feb. 10, 1975, now U.S. Pat. No. 3,933,860, the disclosures of which are incorporated herein by reference.

BACKGROUND OF THE INVENTION

U.S. Pat. No. 3,933,860, issued to David Cheong King Chan on Jan. 26, 1976, and U.S. Pat. No. 4,012,519, issued to David Cheong King Chan on Mar. 15, 1977, disclose the use of a large class of 3-(N-acyl-N-arylamino) lactones and 3-(N-acyl-N-arylamino) lactams as protectant fungicides.

U.S. Pat. No. 4,034,108, issued July 5, 1977, to H. Moser, and U.S. Pat. No. 4,015,648, issued May 24, 1977 to H. Moser, disclose the use of N-(methoxycarbonylethyl)-N-haloacetylanilines as preventive and curative fungicides.

German Patent Publication Nos. 2,643,403 and 2,643,445, published Apr. 7, 1977, disclose the use of N-(alkylthiocarbonylethyl)acetanilides for controlling fungi, particularly those of the class Phycomycetes.

Netherlands Patent Publication No. 152,849, published Apr. 15, 1977, discloses the use of N-(alkoxymethyl)acetanilides as fungicides.

Belgian Pat. No. 867,556, published Nov. 27, 1978, discloses 3-(N-cyclopropyl-carbonyl-N-arylamino)-gamma-butyrolactones.

SUMMARY OF THE INVENTION

It has now been found that 3-(N-cycloalkylcarbonyl-N-arylamino)-gamma-butyrolactones, butyrothiolactones and butyrolactams are effective for the control of fungi, especially for downy mildew fungal infection caused by fungal species of the Peronosporaceae family and late blight fungal infection caused by *Phytophthora infestans*. Some of the compounds of the invention are effective both as protectant fungicides, i.e., they prevent or protect against fungi infections, and as eradicant fungicides, i.e., they eliminate and cure established infections. The compounds of the invention are especially preferred for the control of grape downy mildew.

DESCRIPTION OF THE INVENTION

The compounds of the invention are represented by the Formula (I)

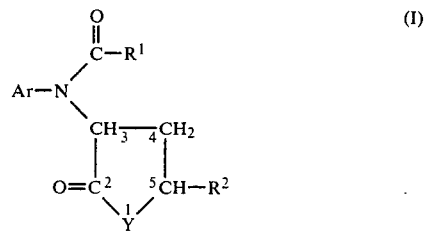

wherein Ar is phenyl, naphthyl, or phenyl or naphthyl substituted with 1 to 4 of the same or different substituents selected from fluoro, chloro, bromo, alkyl of 1 to 4 carbon atoms or alkoxy of 1 to 4 carbon atoms; $R^1$ is cycloalkyl of 3 to 6 carbon atoms, cycloalkyl of 3 to 6 carbon atoms substituted with 1 to 4 of the same or different substituents selected from alkyl of 1 to 4 carbon atoms, fluoro, chloro, bromo, hydroxy or alkoxy of 1 to 4 carbon atoms; and $R^2$ is hydrogen, chloro, bromo, alkyl of 1 to 6 carbon atoms, phenyl or phenyl substituted with 1 to 2 of the same or different substituents selected from fluoro, chloro, bromo or alkyl of 1 to 6 carbon atoms; and Y is O, S or NR wherein R is hydrogen or alkyl of 1 to 4 carbon atoms, with the proviso that when Ar is phenyl or substituted phenyl and $R^1$ is cyclopropyl, Y is not O.

Representative substituted-phenyl groups which Ar may represent are 2-fluorophenyl, 2,4-dichlorophenyl, 3,5-dibromophenyl, 4-methylphenyl, 2,6-diethylphenyl, 4-methoxyphenyl, 4-nitrophenyl, 2,6-dimethyl-4-chlorphenyl, 2,3,6-trimethylphenyl, 2,3,5,6-tetramethylphenyl. Preferred substituted-phenyl Ar groups are phenyl substituted with 1 to 2 of the same or different substituents selected from chloro, bromo, alkyl of 1 to 4 carbon atoms or alkoxy of 1 to 4 carbon atoms. Most preferred substituted-phenyl Ar groups are 2,6-dialkylphenyl, especially 2,6-dimethylphenyl.

Representative substituted-naphthyl Ar groups are 1-naphthyl, 2-naphthyl, 1-methyl-2-naphthyl, 4-methyl-2-naphthyl, 4-methyl-1-naphthyl, 2-chloro-1-naphthyl, 2-methoxy-1-naphthyl, 2,4-dimethyl-1-naphthyl and 2,7-dimethyl-1-naphthyl. Preferred substituted naphthyl Ar groups are 2-alkyl-1-naphthyl groups, especially 2-methyl-1-naphthyl.

Representative cycloalkyl of $R^1$ groups are cyclopropyl, cyclobutyl, cyclopentyl, cyclohexyl, and 4-methylcyclohexyl.

Representative alkyl $R^2$ groups are methyl, ethyl, isopropyl and n-hexyl. Representative substituted-phenyl $R^2$ groups are 2-chlorophenyl, 2,4-dichlorophenyl, 4-methylphenyl and 2,3-dimethylphenyl.

Preferably Ar is phenyl substituted with 1 to 2 of the same or different substituents selected from fluoro, chloro, bromo or alkyl of 1 to 2 carbon atoms, or 2-alkyl-1-naphthyl. The most preferred Ar groups are 2,6-dimethylphenyl or 2-methyl-1-naphthyl.

Preferably $R^1$ is cycloalkyl of 3 to 6 carbon atoms. Most preferably $R^1$ is cyclopropyl when Y=S and cyclopentyl when Y=O.

Preferably $R^2$ is hydrogen or methyl. Most preferably $R^2$ is hydrogen.

The N-phenylamino- and N-substituted phenylamino-thiolactones of the invention may be represented by the formula

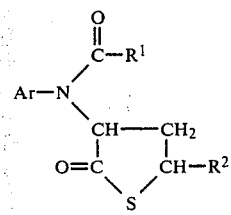

(II)

wherein Ar is phenyl or substituted phenyl as previously defined, and $R^1$ and $R^2$ have the same significance as previously defined. In formula (II), Ar preferably is phenyl substituted with 1 to 2 of the same or different substituents selected from fluoro, chloro, bromo, alkyl of 1 to 4 carbon atoms or alkoxy of 1 to 4 carbon atoms. A preferred class of N-phenylamino- and N-substituted phenylaminothiolactones is that represented by the formula

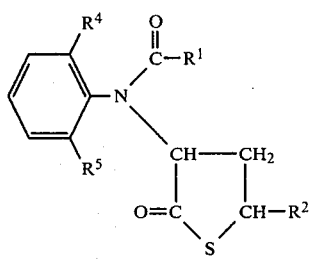

(III)

wherein $R^1$ is cycloalkyl of 3 to 6 carbon atoms, $R^2$ is hydrogen or methyl, and $R^4$ and $R^5$ individually are methyl or ethyl. A particularly preferred compound of formula (III) is that wherein $R^1$ is cyclopropyl, $R^2$ is hydrogen and $R^4$ and $R^5$ are methyl.

The N-phenylamino and N-substituted-phenylaminolactones of the invention may be represented by the formula

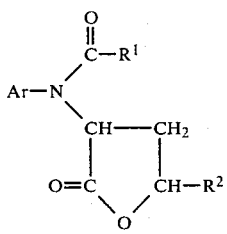

(IV)

wherein Ar is phenyl or substituted phenyl as previously defined, $R^2$ has the same significance as previously defined, and $R^1$ is cycloalkyl of 3 to 6 carbon atoms. A preferred class of N-phenylamino- and N-substituted-phenylaminolactones is that represented by the formula

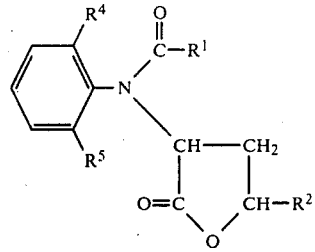

(V)

wherein $R^1$ is cycloalkyl of 4 to 6 carbon atoms, $R^2$ is hydrogen or methyl, and $R^4$ and $R^5$ individually are methyl or ethyl. Preferred compounds of formula (V) are those wherein $R^1$ is cyclopentyl, $R^2$ is hydrogen, and $R^4$ and $R^5$ are methyl.

The N-naphthylamino- and N-substituted naphthylaminolactones and thiolactones of the invention may be represented by the formula

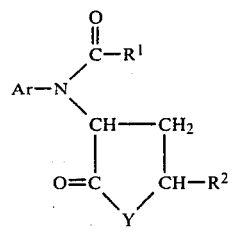

(VI)

wherein Ar is naphthyl or substituted naphthyl, and wherein $R^1$, $R^2$ and Y have the same significance as previously defined. A preferred class of N-naphthyl and N-naphthyl-substituted-aminolactones and thiolactones is that represented by the formula (VII)

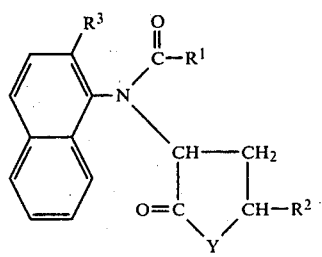

(VII)

wherein $R^1$ is cycloalkyl of 3 to 6 carbon atoms; $R^3$ is hydrogen or alkyl of 1 to 3 carbon atoms; and Y is oxygen or sulfur. Particularly preferred compounds of formula (VII) are those wherein $R^1$ is cyclopropyl, $R^3$ is methyl and Y is oxygen.

Representative compounds of formula (I) include:
3-(N-cyclobutylcarbonyl-N-phenylamino)-gamma-butyrothiolactone;
3-(N-cyclohexylcarbonyl-N-4-chlorophenylamino)-gamma-butyrothiolactone;
3-(N-cyclohexylcarbonyl-N-4-methoxyphenylamino)-gamma-butyrothiolactone;
3-(N-cyclopropylcarbonyl-N-2,6-dimethylphenylamino)-5-methyl-gamma-butyrothiolactone;
3-(N-cyclopentylcarbonyl-N-2,6-dimethylphenylamino)-gamma-butyrothiolactone;
3-(N-cyclopropylcarbonyl-N-3,4-dimethylphenylamino)-gamma-butyrothiolactone;

3-(N-cyclobutylcarbonyl-N-4-methylphenylamino)-5-chloro-gamma-butyrothiolactone;

3-(N-cyclopropylcarbonyl-N-2-methoxyphenylamino)-gamma-butyrolactone;

3-(N-cyclohexylcarbonyl-N-2-methylnaphth-1-ylamino)-5-phenyl-gamma-butyrothiolactone;

3-(N-cyclobutylcarbonyl-N-2-methylnaphth-1-ylamino)-gamma-butyrothiolactone;

3-(N-(2-chlorocyclopropylcarbonyl-N-2-methylnaphth-1-ylamino)-gamma-butyrolactone and 3-(N-(2-methylcyclopropylcarbonyl)-N-2-methylnaphth-1-ylamino)-gamma-butyrolactone;

3-(N-cyclopropylcarbonyl-N-2,6-dimethylphenylamino)-gamma-butyrothiolactone.

The lactones of the invention may be prepared by alkylating an aniline (VIII) with an alpha-halo-gamma-butyrolactone (IX) and subsequently acylating the alpha-(N-arylamino)-gamma-butyrolactone (X) with an acyl halide (XI) to give the 3-(N-acyl-N-arylamino)-gamma-butyrolactone product (I), as depicted by the following equations:

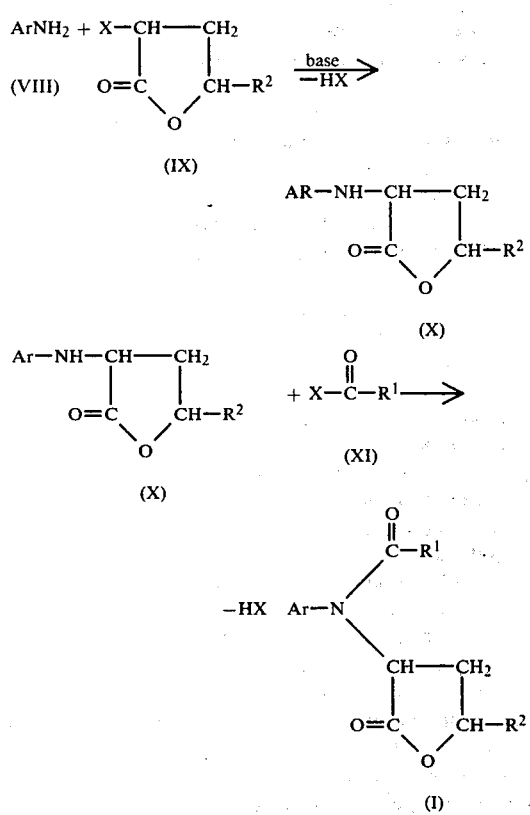

wherein Ar, $R^1$ and $R^2$ have the same significance as previously defined, and X is chloro or bromo.

The alkylation reaction (1) is conducted in the presence of a base. Suitable bases are inorganic alkali metal carbonates such as sodium carbonates or potassium carbonate or organic amines such as trialkylamines, e.g., triethylamine, or pyridine compounds, e.g., pyridine or 2,6-dimethylpyridine. Generally, substantially equimolar amounts of reactants (VIII) and (IX) and the base are employed. In one modification of the reaction, a molar excess of the aniline reactant (VIII) is used as the base, and no additional base is employed. The reaction is conducted in inert organic solvents, e.g., apolar diprotic solvents such as dimethylformamide and acetonitrile and aromatic hydrocarbons such as benzene and toluene, at reaction temperatures varying from 25° C. to 150° C., preferably from 50° C. to 150° C. Water may be employed as a co-solvent. The reaction pressure may be atmospheric, subatmospheric or superatmospheric. However, for convenience of conducting the reaction, the pressure is generally atmospheric. The reaction time will, of course, vary depending upon the reactants and the reaction temperature. Generally, the reaction time is from 0.25 to 24 hours. The product (X) is generally purified by conventional procedures, e.g., extraction, distillation or crystallization, before use in the acylation reaction (2).

Preferred alkylation reaction conditions are given in more detail in the commonly assigned U.S. Pat. No. 4,165,322, the disclosure of which is incorporated herein by reference.

The acylation reaction (2) is conducted by conventional procedures. The reactants (X) and (XI) are generally contacted in substantially equimolar amounts in an inert organic solvent at a temperature of 0° to 100° C. Suitable inert organic solvents include ethyl acetate, methylene dichloride, dimethoxyethane, benzene, etc. The product is isolated and purified by conventional procedures such as extraction, distillation, chromatography, crystallization, etc.

When preparing a butyrolactone product (compounds of Formula (I) wherein Y=O), an organic amine such as a trialkylamine or a pyridine compound may be employed as an acid acceptor. However, when preparing a butyrothiolactone product (compounds of Formula (I) wherein Y=S), an organic amine should not be employed.

Preferred acylation reaction conditions are given in more detail in the commonly assigned application of Richard N. Reynolds, Jr., Stephen D. Ziman and David C. K. Chan, entitled "Acylation of Lactone-Substituted Aniline Compound in the Absence of an Acid Acceptor", Ser. No. 18,489, filed Mar. 8, 1979.

The compounds of Formula (I) wherein $R^2$ is chloro or bromo are generally prepared by chlorinating or brominating the corresponding compound wherein $R^2$ is hydrogen with a chlorinating or brominating agent such as N-bromosuccinimide or N-chlorosuccinimide by conventional procedures, as depicted in the following equation (4):

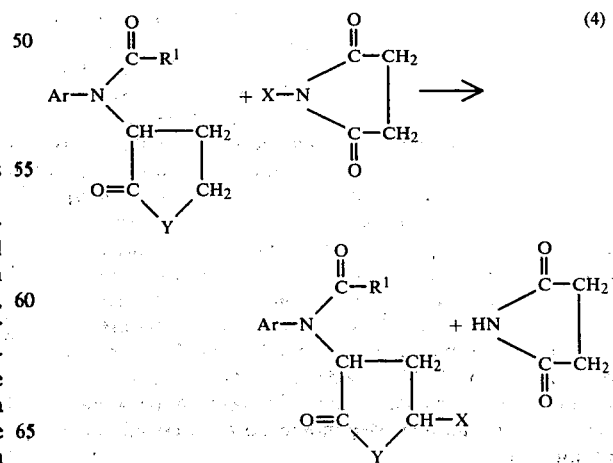

wherein Ar, $R^1$, Y and X are as previously defined.

The thiolactone compounds of the invention may be prepared by cleaving the corresponding lactone (I) with an alkyl mercaptide salt followed by formation of the thiolactone employing a halogenating agent such as phosphorus trichloride, phosphorus pentachloride, thionyl chloride or oxalyl chloride, as depicted by the following equations:

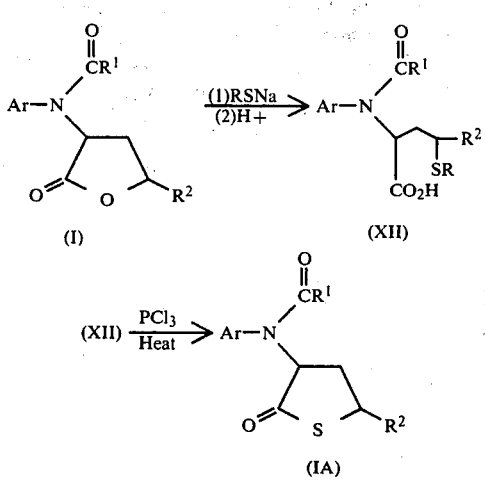

wherein $R^1$, $R^2$ and Ar are as previously defined.

UTILITY

The compounds of the invention are useful for controlling fungi, particularly plant fungal infections. However, some fungicidal compositions of the invention may be more fungicidally active than others against particular fungi. For example, the activity of the preferred compounds of the invention is highly specific for certain fungal diseases such as downy mildews, e.g., *Plasmopara viticola* (grapes) and *Peronospora parasitica* (cabbage and collard), late blights, e.g., *Phytophthora infestans* tomatoes and potatoes), and crown and root rots, e.g., Phytophthora.

The compounds of the invention are particularly useful fungicides because they cure established fungal infections. This permits economical use of the fungicides of the invention, because they need not be applied to plants unless fungal infection actually occurs. Thus, a preventative program of applying fungicides against potential fungal infection is not necessary.

When used as fungicides, the compounds of the invention are applied in fungicidally effective amounts to fungi and/or their habitats, such as vegetative hosts and nonvegetative hosts, e.g., animal products. The amount used will, of course, depend on several factors such as the host, the type of fungus and the particular compound of the invention. As with most pesticidal compounds, the fungicides of the invention are not usually applied full strength, but are generally incorporated with conventional, biologically inert extenders or carriers normally employed for facilitating dispersion of active fungicidal compounds, recognizing that the formulation and mode of application may affect the activity of the fungicide. Thus, the fungicides of the invention may be formulated and applied as granules, as powdery dusts, as wettable powders, as emulsifiable concentrates, as solutions, or as any of several other known types of formulations, depending on the desired mode of application.

Wettable powders are in the form of finely divided particles which disperse readily in water or other dispersant. These compositions normally contain from about 5–80% fungicide, and the rest inert material, which includes dispersing agents, emulsifying agents and wetting agents. The powder may be applied to the soil as a dry dust, or preferably as a suspension in water. Typical carriers include fuller's earth, kaolin clays, silicas, and other highly absorbent, wettable, inorganic diluents. Typical wetting, dispersing or emulsifying agents include, the example: the aryl and alkylaryl sulfonates and their sodium salts, alkylamide sulfonates, including fatty methyl taurides; alkylaryl polyether alcohols, sulfated higher alcohols and polyvinyl alcohols; polyethylene oxides, sulfonated animal and vegetable oils; sulfonated petroleum oils, fatty acid esters of polyhydric alcohols and the ethylene oxide addition products of such esters; and the addition products of long-chain mercaptans and ethylene oxide. Many other types of useful surface-active agents are available in commerce. The surface-active agent, when used, normally comprises from 1% to 15% by weight of the fungicidal composition.

Dusts are freely flowing admixtures of the active fungicide with finely divided solids such as talc, natural clays, kieselguhr, pyrophyllite, chalk, diatomaceous earths, calcium phosphates, calcium and magnesium carbonates, sulfur, lime, flours, and other organic and inorganic solids which act as dispersants and carriers for the toxicant. These finely divided solids have an average particle size of less than about 50 microns. A typical dust formulation useful herein contains 75% silica and 25% of the toxicant.

Useful liquid concentrates include the emulsifiable concentrates, which are homogeneous liquid or paste compositions which are readily dispersed in water or other dispersant, and may consist entirely of the fungicide with a liquid or solid emulsifying agent, or may also contain a liquid carrier such as xylene, heavy aromatic naphthas, isophorone, and other nonvolatile organic solvents. For application, these concentrates are dispersed in water or other liquid carrier, and are normally applied as a spray to the area to be treated.

Other useful formulations for fungicidal applications include simple solutions of the active fungicide in a dispersant in which it is completely soluble at the desired concentration, such as acetone, alkylated naphthalenes, xylene, or other organic solvents. Granular formulations, wherein the fungicide is carried on relatively coarse particles, are of particular utility for aerial distribution or for penetration of cover-crop canopy. Pressurized sprays, typically aerosols wherein the active ingredient is dispersed in finely divided form as a result of vaporization of a low-boiling dispersant solvent carrier, such as the Freons, may also be used. All of those techniques for formulating and applying fungicides are well known in the art.

The percentages by weight of the fungicide may vary according to the manner in which the composition is to be applied and the particular type of formulation, but in general comprise 0.5 to 95% of the toxicant by weight of the fungicidal composition.

The fungicidal compositions may be formulated and applied with other active ingredients, including other fungicides, insecticides, nematocides, bactericides, plant growth regulators, fertilizers, etc.

EXAMPLES

The preparation and fungicidal activity of the compounds of the invention is illustrated by the following examples.

EXAMPLE 1—Preparation of 3-(N-cyclopentylcarbonyl-N-2,6-dimethylphenylamino)-gamma-butyrolactone A 5.7 g. (0.043 mol) sample of cyclopentylcarbonyl chloride was added dropwise to a solution of 8.8 g. (0.043 mol) N-2,6-dimethylphenylamino-gamma-butyrolactone in 100 ml toluene. After completion of the addition, the reaction mixture was refluxed overnight, then washed with water, saturated sodium carbonate solution and again with water, dried over magnesium sulfate and evaporated under reduced pressure to give an oily residue. The residue was crystallized from ethyl ether to give 6.1 g of product, m.p. 109°–113° C. This product is tabulated in Table A as Compound No. 1.

EXAMPLE 2—Preparation of 2-(N-cyclopropylcarbonyl-2,6-dimethylanilino)-4-(t-butylthio)-butanoic acid To 4.2 g. t-butylmercaptan in 100 ml 1,2-dimethoxy ethane was added 2.5 g. sodium methoxide with stirring. A sample of 3-(cyclopropylcarbonyl-2,6-dimethylanilino)-butyrolactone (11.6 g., made as in Example 1) was added to the reaction mixture and stirred at room temperature overnight and poured into ice water.

The mixture was washed with 2×100 ml toluene and the toluene was backwashed with water. The aqueous phase was acidified (pH 1) with 12 N HCl, then extracted twice with methylene chloride. The methylene chloride extracts were washed with water, dried (MgSO₄), filtered and stripped to yield the title product, 10.6 g. (oil).

EXAMPLE 3—Preparation of 3-(N-cyclopropylcarbonyl 2,6-dimethylanilino)-butyrothiolactone The acid produced in Example 2 (10.6 g.) was dissolved in 200 ml methylene chloride in a flask equipped with a condensor, cooled to −20° C. then PCl₃ (6.0 g.) was added dropwise. The exothermic reaction caused the mixture to warm to 36° C. More methylene chloride was added and the mixture was allowed to stand overnight at room temperature, whereupon two phases formed.

The methylene chloride layer was collected, dried (MgSO₄, Silica gel), filtered and stripped. The resultant oil was crystallized in petroleum ether to yield the title product, m.p. 145°–147° C.

The compounds tabulated in Table A were prepared by procedures similar to those of Examples 1–3. The structure of each compound tabulated in Table A was confirmed by nuclear magnetic resonance spectroscopy and/or infrared spectral analysis.

EXAMPLE 4—Tomato Late Blight

Compounds of the invention were tested for the preventative control of the Tomato Late Blight organism *Phytophthora infestans*. Five- to six-week-old tomato (cultivar Bonny Best) seedlings were used. The tomato plants were sprayed with a 250-ppm suspension of the test compound in acetone, water and a small amount of a nonionic emulsifier. The sprayed plants were then inoculated one day later with the organism, placed in an environmental chamber and incubated at 66°–68° F. and 100% relative humidity for at least 16 hours. Following the incubation, the plants were maintained in a greenhouse at 60–80% relative humidity for approximately 7 days. The percent disease control provided by a given test compound was based on the percent disease reduction relative to untreated check plants. The results are tabulated in Table I. In Table I, the test concentration is 250 ppm unless otherwise indicated by the figures in parentheses.

EXAMPLE 5—Celery Late Blight

The celery late blight tests were conducted using celery (Utah) plants 11 weeks old. The celery late blight organism was *Septoria apii*. The celery plants were sprayed with solutions of the candidate toxicant mixed with acetone, water and a nonionic emulsifier. The plants were then inoculated with the organism and placed in an environmental chamber and incubated at 66°–68° F. in 100% relative humidity for an extended period of time (approximately 48 hours). Following the incubation the plants were allowed to dry and then were maintained at a 60–80% relative humidity for approximately 14 days. The percent disease control provided by a given candidate toxicant is based on the percent disease reduction relative to untreated check plants. The results are reported in Table I.

EXAMPLE 6—Grape Downy Mildew Control

The compounds of the invention were tested for the control of the grape downy mildew organism *Plasmopara viticola*. Detached leaves, between 70 and 85 mm in diameter, a 7-week-old *Vitis vinifera* cultivar Emperor grape seedlings were used as hosts. The leaves were sprayed with a solution of the test compound in acetone. The sprayed leaves were dried, inoculated with a spore suspension of the organism, placed in a humid environmental chamber and incubated at 18°–22° C. and about 100% relative humidity. Seven to nine days after inoculation, the amount of disease control was determined. The percent disease control provided by a given test compound was based on the percent disease reduction relative to untreated check plants. The results are tabulated in Table I.

EXAMPLE 7—Tomato Early Blight

Compounds of the invention were tested for the control of the Tomato Early Blight organism, *Alternaria solani conidia*. Tomato (variety Bonny Best) seedlings of 6 to 7 weeks old were used. The tomato plants were sprayed with a 250-ppm solution of the test compound in an acetone-and-water solution containing a small amount of a nonionic emulsifier. The sprayed plants were inoculated one day later with the organism, dried and maintained at 60–80% relative humidity for about 12 days. Percent disease control was based on the percent disease development on untreated check plants. The compounds tested and the results are tabulated in Table I.

EXAMPLE 8—Powdery Mildew

The powdery mildew test was made using bean seedlings (var. Bountiful) with well-developed primary leaves. The pathogen was *Erysiphe polygoni*. The bean seedlings were sprayed with a 250-ppm solution of the test compound in an acetone-water mixture containing a nonionic emulsifier. The treated plants were inoculated one day after spray application of the test compound with the pathogen. The plants were then maintained in a greenhouse at a 60-80% relative humidity and at a temperature of 68°-70° F. The rate of infection on the leaves was made after about 10 days. The percent disease control provided by a given test compound was based on the disease reduction relative to untreated check plants. The results are reported in Table I.

EXAMPLE 9—Leaf Rust

The leaf-rust was made using pinto beans. The pathogen was Uronyces phaseoli tipica. The pinto-bean plants were sprayed with a 250-ppm solution of the test compound in an acetone-water mixture containing a nonionic emulsifier. The treated plants were inoculated thereafter with the pathogen and then incubated in an environmental chamber for approximately 20 hours at 100% relative humidity and a temperature of 68°-70° F. The plants were then removed from the chamber, allowed to dry, and then maintained in a greenhouse at a 60-80% relative humidity. The rate of infection on the leaves was made after about 14 days. The percent disease control provided by a given test compound was based on the disease reduction relative to untreated check plants. The results are reported in Table I.

TABLE I-continued

| | FUNGICIDAL EFFICACY | | | | | |
|---|---|---|---|---|---|---|
| No. | GDM | TLB | CLB | TEB | BR | BPM |
| 6 | 13 | 11 | 0 | 0 | 0 | 98 |

GDM = Grape Downy Mildew
TLB = Tomato Late Blight
CLB = Celery Late Blight
TEB = Tomato Early Blight
BR = Bean Rust
BPM = Bean Powdery Mildew

What is claimed is:
1. A compound of the formula

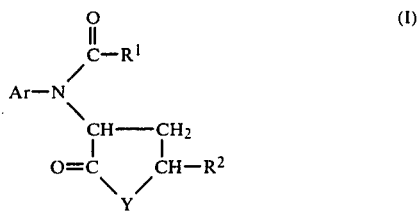

wherein Ar is phenyl, naphthyl, or phenyl or naphthyl substituted with 1 to 4 of the same of different substituents selected from fluoro, chloro, bromo, alkyl of 1 to 4 carbon atoms or alkoxy of 1 to 4 carbon atoms; $R^1$ is cycloalkyl of 3 to 6 carbon atoms, cycloalkyl of 3 to 6 carbon atoms substituted with 1 to 4 of the same or different substituents selected from alkyl of 1 to 4 carbon atoms, fluoro, chloro, bromo, hydroxy or alkoxy of 1 to 4 carbon atoms; and $R^2$ is hydrogen, chloro, bromo, alkyl of 1 to 6 carbon atoms, phenyl or phenyl substituted with 1 to 2 of the same or different substituents selected from fluoro, chloro, bromo and alkyl of 1 to 6 carbon atoms; and Y is S.

TABLE A

Compounds of the Formula

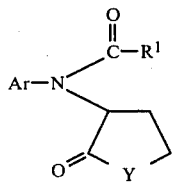

| | | | | | ANALYSIS | | | | | |
|---|---|---|---|---|---|---|---|---|---|---|
| | | | | mp | C | | H | | N | |
| No. | Ar | $R^1$ | Y | °C. | Calc | Fd | Calc | Fd | Calc | Fd |
| 1 | 2,6-(CH$_3$)$_2$φ | ⬠ | O | 109–113 | 71.73 | 72.78 | 7.69 | 7.94 | 4.65 | 4.67 |
| 2 | 2,6-(CH$_3$)$_2$φ | ☐ | O | 119–120 | 71.06 | 70.87 | 7.37 | 7.54 | 4.88 | 4.75 |
| 3 | 2,6-(CH$_3$)$_2$φ | ⬡ | O | 162–163 | 72.35 | 73.37 | 7.98 | 8.36 | 4.44 | 4.48 |
| 4 | 2,6-(CH$_3$)$_2$φ | △ | S | 145–147 | 66.40 | 66.97 | 6.62 | 6.75 | 4.84 | 5.4 |
| 5A* | 1-CH$_3$-naphthyl | △ | O | 186–190 | 73.77 | 73.79 | 6.19 | 6.43 | 4.53 | 4.47 |
| 5B* | 1-CH$_3$-naphthyl | △ | O | 139–142 | 73.77 | 74.35 | 6.19 | 6.29 | 4.53 | 4.49 |
| 6 | 2,6-(CH$_3$)$_2$φ | △ | NCH$_3$ | 113–114 | 71.30 | 70.35 | 7.74 | 7.74 | 9.78 | 9.69 |

*A and B rotamers.

TABLE I

| | FUNGICIDAL EFFICACY | | | | | |
|---|---|---|---|---|---|---|
| No. | GDM | TLB | CLB | TEB | BR | BPM |
| 1 | — | 81 | 19 | 0 | 0 | 10 |
| 2 | — | 50 | 19 | 0 | 0 | 0 |
| 3 | — | 0 | 7 | 0 | 0 | 4 |
| 4 | 98 | 71 | 19 | 0 | 29 | 4 |
| 5A | 99 | 6 | 44 | 21 | 0 | 0 |
| 5B | 99 | 13 | 44 | 56 | 0 | 23 |

2. The compound of claim 1 represented by the formula

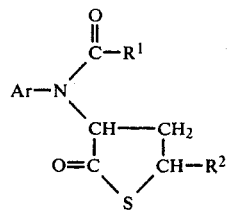

(II)

wherein Ar is phenyl or substituted phenyl as defined in claim 1 and $R^1$ and $R^2$ have the same significance as defined in claim 1.

3. The compound of claim 2 wherein Ar is phenyl substituted with 1 to 2 of the same or different substituents selected from fluoro, chloro, bromo, alkyl of 1 to 4 carbon atoms or alkoxy of 1 to 4 carbon atoms.

4. The compound of claim 3 represented by the formula

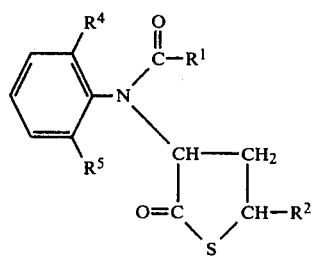

(III)

wherein $R^1$ is cycloalkyl of 3 to 6 carbon atoms, $R^2$ is hydrogen or methyl, and $R^4$ and $R^5$ individually are methyl or ethyl.

5. The compound of claim 4 wherein $R^1$ is cyclopropyl, $R^2$ is hydrogen and $R^4$ and $R^5$ are methyl.

6. The compound of claim 1 represented by the formula

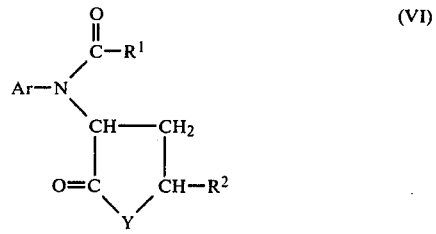

(VI)

wherein Ar is naphthyl or substituted naphthyl as defined in claim 1, and $R^1$, $R^2$ and Y have the same significance as defined in claim 1.

7. The compound of claim 1 represented by the formula

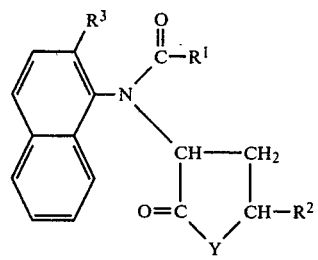

(VII)

wherein $R^1$ is as defined in claim 1; $R^3$ is hydrogen or alkyl of 1 to 3 carbon atoms; and Y is sulfur.

8. A method of the control of fungi which comprises contacting said fungi or their habitats with a fungicidally effective amount of a compound of the formula defined in claim 1.

9. A method for controlling the growth of *Phytophthora infestans* fungi which comprises applying to said fungi or their habitats a fungicidally effective amount of a compound of the formula defined in claim 1.

10. A method for controlling the growth of *Plasmopara viticola* fungi which comprises applying to said fungi or their habitats a fungicidally effective amount of a compound of the formula defined in claim 1.

11. A fungicidal composition comprising a biologically inert carrier and a fungicidally effective amount of a compound of the formula defined in claim 1.

* * * * *